United States Patent [19]

Reichert

[11] Patent Number: 4,556,557

[45] Date of Patent: Dec. 3, 1985

[54] METHOD AND COMPOSITION FOR COMBATING SNORING, AND THE USE OF SURFACE ACTIVE SUBSTANCES FOR THE PREPARATION OF SAID COMPOSITION

[76] Inventor: Dietrich Reichert, Mühlenwiese 51, D-2806 Oyten-Schaphusen, Fed. Rep. of Germany

[21] Appl. No.: 514,182

[22] Filed: Jul. 15, 1983

Related U.S. Application Data

[63] Continuation-in-part of Ser. No. 327,585, Dec. 4, 1981, abandoned.

[30] Foreign Application Priority Data

Dec. 6, 1980 [DE] Fed. Rep. of Germany ....... 3046125
Dec. 10, 1980 [DE] Fed. Rep. of Germany ....... 3046484

[51] Int. Cl.$^4$ ............... A61K 37/48; A61K 33/14; A61K 31/355; A61K 31/235
[52] U.S. Cl. ...................... 424/94; 424/153; 514/458; 514/535; 514/642; 514/725; 514/758; 514/785
[58] Field of Search ................ 424/153, 192, 172, 170

[56] References Cited

U.S. PATENT DOCUMENTS 2,989,437 6/1961 Wrubel et al. ...................... 424/181
4,259,323 3/1981 Ranucci ............................... 424/153

FOREIGN PATENT DOCUMENTS 2805248 8/1978 Fed. Rep. of Germany ...... 424/326
2379508 9/1978 France ................................ 424/172
1599159 2/1977 United Kingdom ................ 424/326

OTHER PUBLICATIONS

Modern Drug Encyclopedia, Reuben H. Donnelly Corp., 9th Ed., New York, 1964.
"Unlisted Drugs", vol. 24, No. 11, 1972.
"Vidal" sheet listing pharmaceuticals.
Michael Struck, Report, Of the Evaluation of Surface-Active ... Substances ... as Anti-Snoring Agent, Dec. 21, 1983 (With Translation).
Albic, "NORON helpt tegen snurken", adv't, 1983.

Primary Examiner—Albert T. Meyers
Assistant Examiner—John W. Rollins, Jr.
Attorney, Agent, or Firm—Curtis, Morris & Safford

[57] ABSTRACT

A composition for overcoming snoring as well as a process for its use is disclosed. The composition according to the invention contains a surface active substance, a preserving agent and/or a substance acting bactericidally or fungicidally on the mucous membranes and optionally a substance for softening the mucous membranes in physiological common salt solution as well as optionally further additives which are compatible with the mucous membranes.

11 Claims, No Drawings

METHOD AND COMPOSITION FOR COMBATING SNORING, AND THE USE OF SURFACE ACTIVE SUBSTANCES FOR THE PREPARATION OF SAID COMPOSITION

This is a continuation-in-part application of application Ser. No. 327,585, filed Dec. 4, 1981, now abandoned.

BACKGROUND OF THE INVENTION

Snoring is a phenomenon which is based on rhoncus breathing, which may occur among human beings during sleep. Due to the strain which snoring may place upon other human beings, many attempts have been made to provide a remedy for this phenomenon.

The cause of snoring in normal healthy people are believed to be obstructions (unevenness) in the area of the upper respiratory tracts. During inhalation and exhalation, the air is led via complex flow channels. Unevennesses in these areas lead necessarily to turbulences in the air flow. These cause impediments to breathing, which are below the consciousness threshold. The impediments in the flow channels and the turbulences caused thereby have the consequence that locally a low pressure area (suction) is formed. This leads to fluttering motions of soft, relaxed structures in the area of the air flow channels. In particular the soft gums are moved backward and forward by the above-mentioned turbulences. Although numerous investigations have been carried out to prevent snoring, as yet they have not led to the desired success. These efforts have been based on compositions which were built up on chemotherapeutics or antibiotics, vasoactive substances, corticoids or on antihistaminics. These compositions, however, have either proved to be not effective enough to prevent snoring over long periods, or when taken over lengthy periods they have led to damage to the mucous membranes of the nose and of the pharynx. This also applies to the known tests in earlier days using essential oils, such as for example menthol, camomile, eucalyptus oil, etc.

DESCRIPTION OF THE PRIOR ART

Robin analyses the phenomenon of snoring in Proc. Roy. Soc. Med. 61, 575-582 (1968). On page 581 in the paragraph linking columns 1 and 2 of the article he notes that certain factors such as smoking may lead to nasal congestion, and that with "minor degrees of mucosal congestion simple decongestive nasal drops may be allowed and prove succesful". In the medical language "nasal or mucosal congestion" specifies a pathological gathering of blood in the nose or in the nasal mucous membranes (the so-called concha).

People who suffer from such a pathological state with the corresponding symptoms may be given decongestive nasal drops according to Robin. Typical decongestive preparations are described e.g. in U.S. Pat. No. 2 989 437, which however gives no indication that the snoring is influenced, and in which the concept "nasal decongestant composition" is used in the title. With the administration of decongestive nasal drops in the conventional way the blood congestion in the concha can be reduced, and thereby a restriction of the concha attained. For example in U.S. Pat. No. 2 989 437 this is based on the vasoconstringent action of the phenylephrine within the decongestive composition. Nose drops of the decongestive type are widely known and are distinguished by the fact that they build on a vasoactive component. This vasoactive component normally causes a vasoconstriction. The modus operandi of decongestive products is described for example in "Laryngoscope" 91, 1614–1621 (1981).

In nose medicine also a differentation is made between preparations which contain decongestive substances, and those which are otherwise composed, e.g. on the basis of chemotherapeutics, antihistaminics etc., or on the basis of surface active substances. This emerges clearly from "Hals-Nasen-Ohren-Heilkunde", Handbook, Vol. 1, "Obere und untere Luftwege", 1964, Georg Thieme Verlag, Stuttgart, in which the various groups of nasal preparations are described with clear demarcation from each other. Thus on page 213 et seq. under the heading "Groups of Medicines" firstly those are described which contain the chemotherapeutics, antibiotics and tuberculostatics. Then on page 218 there follows the preparations containing vasoactive substances. The decongestive active substances described include adrenaline and its derivatives, such as noradrenaline, ephedrine, naphazoline, tetrahydrozoline, xylometazoline, methylamino-ethanol-phenol compounds, amphetamine, phenyl-propanolamine, cyclopentamine, and many others. Then on page 222 et seq. the preparations are listed which contain surface active substances.

The administration of decongestive preparations moreover is not a suitable method for the combating of the noise of snoring. This is because due to the decongestive substances being constantly used, side effects, rebound effects and other disturbances occur. Lastly it was possible to show by orientation tests that typical decongestive preparations either have no effect or no adequate effect against snoring.

OBJECT OF THE INVENTION

It is the object of the present invention to make available a method and a composition to overcome snoring, by the use of which even cases of heavy snoring can be prevented or greatly alleviated without any harmful side-effects caused by adverse effects on the mucous membranes of the nose and pharynx. Namely the so-called common snoring which is largely present with completely healthy people (in nose and mouth area) and therefore is essentially a sound phenomenon shall be overcome.

According to one aspect of the object of the present invention these effects shall be accomplished by providing compositions which do not contain decongestive active ingredients. According to another aspect of the object of the present invention the compositions shall be free also from chemotherapeutics and antibiotics.

DETAILED DESCRIPTION OF THE INVENTION

These objects are accomplished by the invention in that a method and a composition are made available which comprises
(a) a surface active substance and
(b) an agent selected from the group consisting of a preserving agent and substances acting bactericidally or fungicidally on the mucous membranes,
in physiological common salt solution.

By the method of use of the composition according to the invention surprisingly snoring and namely common-snoring can be prevented or reduced in a large percentage of afficted persons when it is applied to the mucous membranes of the nose and pharynx of the persons concerned, whereby it keeps the mucous membranes of the nose and pharynx moist and where possible it cleanses them of dry mucous.

The method and composition according to the invention also ensure in several ways the smoothing of the surfaces which delimit the flow channels. The mucous membranes which are exposed to daily strain from noxious agents can recover, tough mucous liquifies and again expands in the physiologically necessary manner. Connected therewith is an increase of the normal functions to the point of optimal normal functioning.

Thus the effects of the agent according to the invention are believed to be based on the fact that snoring, which is caused inter alia by the drying out of the mucous membranes of the nose and pharynx, is prevented by the moistening as well as the possible purification of the mucous membranes.

The moistening of the mucous membranes is attained in the case of the composition according to the invention by a physiological common salt solution in connection with at least one surface active agent. It has been possible to show that the adjustment of the physiological common salt solution (i.e., isotonic normal saline solution) in respect of its sodium chloride content is not so critical, i.e. that the common salt solution can also contain sodium chloride in concentrations deviating from the physiological conditions.

The surface active substances play a substantial part in the composition of the invention, in order to maintain contact and to improve it between the physiological common salt solution and the mucous membranes of the nose and pharynx. Here it is primarily important that the surface active substances should be compatible with the mucous membranes. It is preferable for the surface active substances to be in a position to remove dry mucous residues on the mucous membranes of the nose and pharynx.

According to the invention, anionic, cationic, amphoteric and non-ionic surface active compounds are in question. The important prerequisite for the surface active substances is their compatibility with mucous membranes. In addition, they should have a pleasant smell and taste.

The non-ionic surface active substances have been shown to be especially preferred. Since they do not have any salt forming groups, they are not reduced by bivalent or multivalent cations, so that they can be used preferably in combination with other substances.

According to the invention, the preferable surface active substances have been shown to be polyoxyalkylene derivatives of the sorbitanesters, i.e. sorbitanesters in which the free hydroxyl groups are etherified with a certain number of ethylenoxide molecules. The most useful of these ethers are those on which about 20 moles ethyleneoxide and more are condensed. Similarly the analogous esters of sorbitol and mannitol in which free hydroxyl groups are etherified with ethyleneoxide molecules can be utilized.

Polysorbate 80 (Tween 80), a non-ionic substance is an especially suitable product, which consists essentially of a monooleate ester of sorbitan and sorbitol which is etherified with about 90 moles ethyleneoxide.

Tween 20 is also suitable; it comprises a polyoxyethylene derivative from sorbitanhydride, contains a lauryl radical and is etherified with about 20 oxyethylene groups. Also suitable are polyoxyethylenesorbitan monopalmitate (Tween 40) and polyoxyethylenesorbitan monostearate (Tween 60).

Further surface active substances such as Triton, e.g. from the firm Rohm & Haas, Philadelphia, USA, are suitable as the surface active substances. Particularly suitable is Triton WR 1339.

Also suitable is lecithin, as in the group of such type of compounds normally a hydrophilic glycerino phosphoric acid choline moiety and hydrophobic alkyl groups of fatty acids exist. Other examples of such type are tenside fatty alcohols and their derivatives.

Other embodiments of appropriate surface active substances which can be used in accordance with the invention are fatty acid esters of oxyethylated pentaerithritol.

According to the invention the surface active substances are largely free of undesirable smell or taste. It is especially advantageous when the surface active substance used also exercises a stimulating effect on the cilia.

The surface active substance is added to the agent according to the invention in a concentration of preferably from 0.05 to 2% by weight, based on the total weight of the composition. In most cases it is of advantage to work with lower concentrations of the surface active agent. For this purpose the surface active agent is preferably added in a concentration of from 0.1 to 0.5% by weight, while from 0.15 to 0.30% by weight are particularly preferred.

Further it may be of advantage that a preserving agent is added to the composition according to the invention. This is especially necessary in order to prevent a microbial growth in the composition itself, especially after it has been opened.

It is especially preferable if the added preserving agent can additionally act upon the mucous membranes of the nose and pharynx cavities bactericidally and/or fungicidally. To the extent that the preserving agent does not exert this effect or does not do so adequately, a suitable substance which acts upon the mucous membranes of the nose and pharynx bactericidally and/or fungicidally may be added to the composition according to the invention as a mucous membrane disinfectant.

As the preserving agent, those which are in general use in pharmaceutical preparations can be added, when they prevent microbial growth and are not harmful in the use according to the invention. For example, ethanol, esters of the p-hydroxybenzoic acid, 2-phenoxyethanol, benzoic acid and its salts, sorbic acid and its esters etc.

Suitable mucous membrane disinfectants, which can take effect both as disinfectant agents as well as antiseptics, are acridine and quinoline derivatives, quaternary ammonium compounds as well as compounds with amidine structures.

According to the invention particularly good results are obtained using benzalkonium chloride, which is a mild disinfectant compatible with the mucous membranes. It prevents any possible rapid new mucous obstruction, in that it wards off irritation due to impurities in the mucous membranes of the nose, and thereby reduces the irritation. Excessive mucous formation rapidly occurring would again trigger off the snoring, especially in connection with the drying possibilities of the mucous.

Apart from the above mentioned benzalkonium chloride, other quaternary amines, to the extent that they are not incompatible with the mucous membranes, are suitable as disinfectants in the composition according to the invention.

The use of benzododecinium has also shown itself to be suitable as a further mucous membrane disinfectant.

As the fungostatically effective agent, it has been found that the addition of chlorobutanol, a compound which has both bactericidal as well as fungostatic effects, is suitable.

The preserving agents are added optionally to the compositions of the invention together with bactericidally or fungicidally effective substances in a concentration of from 0.01 to 4% by weight, based on the total weight of the composition. Preferably the concentration of the bactericidal and fungostatic compounds amounts to 0.01 to 0.05 g, based on 1000 ml of the composition according to the invention.

Moreover the composition of the invention may contain preferably substances which exercise a flexing or softening influence on the mucous membranes of the nose and pharynx.

The object of this softening agents for the mucous membranes is to prevent the formation of microfissures in them or to cause their decline.

For this purpose the polyalcohols are suitable, which prevent the surface drying of the mucous membranes and in addition also reduce the surface tension of the water phase. The suitable polyalcohols include ethylene glycol, diethylene glycol, propylene glycol, dipropylene glycol, glycerol, diglycerol, butyl glycol-1,3 and sorbite. To the extent that the surface active substance is a polyalcohol itself exhibiting the above properties an additional softening agent is not required. If such agent is used, however, glycerol and sorbitol are especially suitable.

In addition the use of panthenol as a means for flexing the mucous membranes has been shown to be advantageous. Panthenol is compatible with the mucous membranes and has an effect similar to that of pantothenic acid. Simultaneously panthenol has a regenerating surface effect on the mucous membranes.

The substances for softening or flexing the mucous membranes may be contained in the composition of the invention in a concentration of preferably from 0.1 to 1% by weight based on the total weight of the composition. The preferred concentration range is from 0.2 to 0.4% by weight.

In addition substances which are compatible with the mucous membranes, which prevent the formation of microfissures or favor the removal of disturbing substances, can be added to the composition of the invention.

These additives should primarily contribute to the removal of deposits or the formation of tough mucous on the mucous membranes, or to the prevention thereof. Therefore, it may be sometimes advantageous to add an enzyme preparation which is compatible with mucous membranes and which promotes the dissolution of disturbing substances of the composition of the invention. The suitable enzyme preparations are especially the hydrolases, lipases and proteases. Here it is preferable to add enzyme products which, in the pH range to be found on the mucous membranes of the nose and pharynx, have at least approximately their pH optimum and are as far as possible stable under the prevailing conditions.

Also vitamins such as vitamin A in an amount of about 15,000 IE/ml, and vitamin E, e.g. as acetate in an amount of about 20 mg/l are suitable as additives compatible with the mucous membranes.

In addition it is advantageous to add to the composition of the invention substances compatible with mucous membranes such as the serolytics, e.g. acetyl cystein as well as compounds from the range of sympathomitetics, e.g. 2-amino-heptane, forthane, 2-amino-6-methyl heptane. Also substances like menthols, camomille, eucalyptus oils etc., can be useful.

The formulations below are intended to define the agent of the invention more precisely, but without limiting it to the examples listed here. From the foregoing and the below examples it becomes clear that the compositions according to this invention preferably do not contain vasoconstrictive agents, hormones and antibiotics. Also, if desirable, flavoring agents, sweeteners and other types of additives conventionally used to favorably influence the taste and smell of nasal preparations may be included.

| Prescription 1 | |
| --- | --- |
| sodium chloride | 8.5 to 9.5 g |
| surface active agent (Polysorbate 80) | 1.3 to 3.5 g |
| glycerol | 2.0 to 4.0 g |
| ethyl alcohol 90° (vol/vol) | 3.0 to 8.0 g |
| panthenol | 1.5 to 4.0 g |
| benzalkonium chloride | 0.01 to 0.15 g |
| demineralized water up to | 1000 ml |
| Prescription 2 | |
| Polysorbate 80 | 2 g |
| glycerol | 3 g |
| ethyl alcohol 90° (vol/vol) | 6 g |
| benzalkonium chloride | 0.02 g |
| filled up with physiological common salt solution to | 1000 ml |
| Prescription 3 | |
| lecithin | 2.5 to 4 g |
| dodecinium chloride | 0.3 g |
| eucalyptus oil | 1 g |
| fatty alcohol emulsifier | (trace) |
| filled up with physiological common salt solution to | 1000 ml |

The invention also comprises a process for the use of the inventive composition for overcoming snoring, which consists of applying the composition to the mucous membranes of the nose and pharynx of the person concerned with the aid of a suitable device and in adequate quantities. To achieve the effect desired, relatively small amounts of the composition of the invention are sufficient, e.g. about 0.5 to 10 ml, preferably 1.0 to 2.0 ml. The composition of the invention is introduced or dripped into each nostril using a suitable instrument or device, so that the liquid is applied to the mucous membranes of the nose and pharynx. Suitable devices to implement this process are known. For example the composition can be applied by an aerosol device, by an atomizer, a rinsing pipette with individual ampules or individual dose ampules with pipette, or by pipette bottles which contain the composition. The composition is taken in the evening before going to bed, either lying down or standing with head bent backward. The application can be repeated during the night.

The tests carried out on human beings have shown that the composition does not produce any incompatibilities, not even when used over long periods, because the components are not toxic in the concentrations stated above and the relevant components have already been used individually in rhinology.

In addition the tests have shown that the composition according to the invention is particularly effective and that the snoring is either wholly prevented or at least is greatly reduced.

What is claimed is:

1. A method of combating snoring, which comprises administering to a snoring victim's nasopharyngeal mucous membranes, shortly prior to his or her retiring for sleep, a composition containing
   (a) 0.05 to 2% by weight of a non-ionic surface active substance compatible with the mucous membranes and largely free of undesirable smell and taste and
   (b) 0.01 to 4% by weight of a pharmaceutically acceptable agent selected from the group consisting of a preserving agent and substances acting bactericidally or fungicidally on the mucous membranes,
   in a physiological common salt solution.

2. The method according to claim 1, wherein the composition further contains 0.1 to 1% by weight of a softening compound for softening the mucous membranes.

3. The method according to claim 1, wherein the surface active substance is selected from the group consisting of fatty acid ester of oxyethylated sorbitol, sorbitan, pentaerithritol, lecithins and oxyethylated octylphenol formaldehyde polymers.

4. The method according to claim 1, wherein the surface active substance is a polyoxyalkylene ester of sorbitan.

5. The method according to claim 4, wherein the surface active substance is a polyoxyethylene sorbitan monocarboxylate.

6. The method according to claim 4, wherein the surface active substance is a polyoxyethylene sorbitan monooleate.

7. The method according to claim 1, wherein the preserving agent is a substance selected from the group consisting of ethanol, esters of p-hydroxybenzoic acid, 2-phenoxy-ethanol benzoic acid and its salts, and sorbic acid and its esters.

8. The method according to claim 1, wherein the composition contains as said agent benzalkonium chloride.

9. The method according to claim 1, wherein the composition contains as said agent chlorobutanol.

10. The method according to claim 2, wherein the softening compound is at least one substance selected from the group consisting of glycerol, sorbitol and panthenol.

11. The method according to claim 1, wherein the composition contains additionally at least one substance selected from the group consisting of vitamin A, vitamin E, hydrolases, lipases and proteases.

* * * * *